United States Patent [19]

Latimer

[11] Patent Number: 4,685,334
[45] Date of Patent: Aug. 11, 1987

[54] METHOD FOR ULTRASONIC DETECTION OF HYDROGEN DAMAGE IN BOILER TUBES

[75] Inventor: Paul J. Latimer, Lynchburg, Va.
[73] Assignee: The Babcock & Wilcox Company, New Orleans, La.
[21] Appl. No.: 823,034
[22] Filed: Jan. 27, 1986
[51] Int. Cl.⁴ .............................................. G01N 29/04
[52] U.S. Cl. ........................................ 73/599; 73/622
[58] Field of Search ................. 73/599, 622, 637, 638, 73/643, 588

[56] References Cited

U.S. PATENT DOCUMENTS 3,512,400  5/1970  Lynnworth .......................... 73/599
4,092,868  6/1978  Thompson et al. .................... 73/638
4,307,616  12/1981  Vasile .................................. 73/643

OTHER PUBLICATIONS

"Inspection for Hydrogen Damage in Boiler Waterwall Tubes", Singh; *Materials Evaluation*, Sep. 1985.
"Ultrasonic Velocity Ratio Method for Detecting & Evaluating Hydrogen Attack in Steels", Watanabe et al, *ASTM*, pp. 153–165, May 22–24, 1984.
Failures & Inspection of Fossil-Fired Boiler Tubes: 1983 Conference & Workshop, CS-3272, Contract WS 82-101, Dec. 1983, Articles:
a. "Inspection for Hydrogen Damage in Waterwall Tubes Using Ultrasonic Techniques", Sloat et al.
b. "Mitigating Forced Outages by Selective Replacement of Boiler Tubes", Loper et al.
c. "Working Group on Hydrogen Damage, Pitting and Deposits", Freeh et al.

*Primary Examiner*—Anthony V. Ciarlante
*Attorney, Agent, or Firm*—Vytas R. Matas; Robert J. Edwards

[57] ABSTRACT

Angle-beam ultrasonic shear-waves, which are introduced via a pitch-catch technique in the axial and circumferential directions of a boiler tube, are used to detect the presence of hydrogen damage in boiler tubes.

6 Claims, 5 Drawing Figures

METHOD FOR ULTRASONIC DETECTION OF HYDROGEN DAMAGE IN BOILER TUBES

BACKGROUND OF THE INVENTION

This invention relates to the ultrasonic detection of hydrogen damage in boiler tubes and, more particularly, to a pitch-catch method of transmitting angle-beam ultrasonic shear-waves axially and circumferentially of the axis of a boiler tube to detect hydrogen damage.

In recent years, a number of boiler tube failures have been attributed to hydrogen damage. Hydrogen damage is caused by the diffusion of hydrogen through steel reacting with carbon to form methane, which builds up local stresses at the grain boundaries, forming microfissures that propagate radially from the inner waterside surface of the tube toward the fireside surface.

Hydrogen damage is usually associated with a corrosive process and some type of triggering mechanism such as overheating. The hydrogen typically forms under a corrosion deposit. Hydrogen is formed by a corrosive reaction, between the tube metal and the corrosion deposit, that acts as a triggering mechanism which causes water to dissociate into hydrogen. The hydrogen more readily diffuses into the metal through the corrosion deposit. Once in the metal, the hydrogen interacts with carbon in the steel to form methane. The larger methane molecules cannot diffuse out of the metal. Consequently, high pressure areas are formed which create microfissuring at the grain boundaries and, ultimately, a form of tube failure, known as blowout, that is characterized by a thick-lipped fracture.

Some ultrasonic techniques have been used to detect hydrogen damage or corrosion in fossil boiler tubes with only limited success. Known ultrasonic techniques, however, have been unable to detect hydrogen damage underneath welds and field tests indicate that damage underneath the weld does not always extend beyond the weld itself. The inability to detect localized areas of hydrogen damage underneath welds has been a major concern. Visual inspection of welds or total replacement of tubes with a failure history, for this reason, have been undertaken at great inconvenience and expense to avoid tube failures due to hydrogen damage at weld areas.

SUMMARY OF THE INVENTION

Ultrasound is used to detect hydrogen damage in boiler tubes, in accordance with the invention, by measuring the attenuation in the amplitude of angle-beam ultrasonic shear-waves that occurs as waves pass through the damaged area.

The ultrasound is, in one embodiment of the invention, introduced and received in a reflected pitch-catch mode in the axial and circumferential directions of the boiler tube.

The technique of the invention contemplates, in one aspect of the first embodiment, the utilization of an ultrasonic search unit arrangement in which transmitting and receiving transducers are arranged at axially aligned and spaced positions on the outer surface of the tube. The ultrasonic waves are transmitted by the transmitting transducer at an oblique angle of incidence, with respect to the tube axis, and received at an oblique angle of emergence by the receiving transducer. In accordance with another aspect of the first embodiment of the invention, transmitting and receiving transducers are arranged at circumferentially aligned and spaced positions on the outer surface of the tube. The ultrasonic waves are transmitted from the transmitting transducer circumferentially within the tube wall along a segment of the tube and received by the receiving transducer.

The circumferential technique allows the rapid scanning of straight sections of boiler tubing for damage. Both the axial and circumferential techniques are complimentary. Both the axial and circumferential techniques can be used to detect the same damaged area from different directions of sound propagation. The use of both techniques increases the confidence level of the results.

In accordance with a feature of the first embodiment of the invention, the transmitting and receiving transducers are located symetrically about a weld in a boiler tube. Ultrasound is introduced on one side of the weld and received on the other side. The axial technique has been found to be particulary effective in the detection of hydrogen damage to welded areas.

In accordance with a second embodiment of the invention, an electromagnetic acoustic transducer (EMAT) is utilized to introduce an angle-beam shear-wave into the boiler tube which is transmitted circumferentially through the wall of the tube and received by the same transducer. Relative attenuation is compared to relative attenuation of an undamaged tube to detect the presence of hydrogen damage.

BRIEF DESCRIPTION OF THE DRAWING

In the accompanying drawings, forming a part of this specification, and in which reference numerals shown in the drawings designate like or corresponding parts throughout the same.

DETAILED DESCRIPTION

Figure 1:
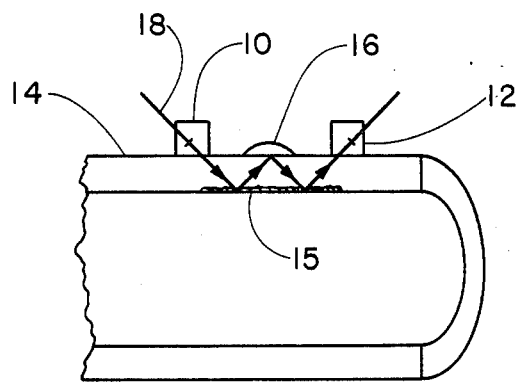
FIG. 1 represents a schematic side view of the area of a boiler tube on which an axially aligned and spaced transmitting transducer and a receiving transducer have been mounted to carry out the method of the invention.

FIG. 1 schematically illustrates angle-beam contact type ultrasonic search unit arrangement which comprises a sending transducer 10 and receiving transducer 12 mounted to the outside of a tube 14 on opposite sides of a weld 16.

Figure 2:
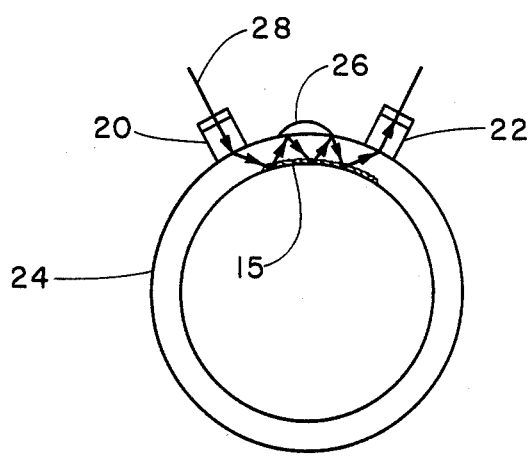
FIG. 2 is a schematic end view of a tube in which circumferentially aligned and spaced transmitting and receiving transducers have been mounted to carry out the method of the invention.

FIG. 2 illustrates an angle-beam contact type search unit arrangement comprising a sending transducer 20 and a receiving transducer 22 mounted at circumferentially spaced positions on the outer surface of a tube 24 on opposite sides of a weld 26.

The transducers 10, 12, 20, 22, which are shearwave angle-beam transducers, are typically mounted in a search unit that comprises wedges (not shown) having inclined surfaces to which the transducer is mounted to provide a desired angle of incidence or reception of the ultrasonic sound waves which are transmitted through the tube being tested. The tube contact surface of the search units is provided with a curvature which corresponds to and fits the curvature of the tube 14. For practicing the techniques disclosed herein, the search units may comprise suitable known angle-beam contact type constructions for circumferential and longitudinal tube inspections.

In operation, as shown in FIG. 1, transmitting transducer 10 and receiving transducer 12 are arranged on the outer surface of the tube 14 in axial alignment. In the illustrated arrangement, the transducers 10, 12 are positioned at equal distances from opposite sides of the weld. The differences in relative attenuation in scanning occuring in an undamaged area and a hydrogen damaged area are used to detect hydrogen damge. Relative attenuation is variable throughout a damaged area. Hence, as used herein, attenuation refers to the average relative drop in signal amplitude over the damaged area.

Figure 3:
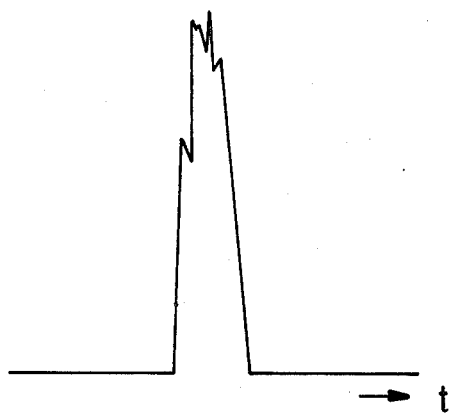
FIG. 3 shows a wave form of a signal from an undamaged area of a boiler tube using the axial angle-beam pitch-catch technique of the invention.
Figure 4:
FIG. 4 is a wave form of a signal from a hydrogen damged area of the boiler tube of FIG. 3 using the axial angle-beam pitch-catch technique of the invention.

The ultrasonic transmitting transducer 10 is thus energized to transmit shear-waves along path 18 into the tube 14 at a predetermined beam-angle, preferably sixty degrees for steel tubes, relative to the tube surface. The use of two 5 MHz miniature sixty-degree angle-beam transducers with a ¼-inch active element is preferred. The receiving transducer 12 receives the wave, which if hydrogen damage is present, has been subjected to attenuation. A comparison of the signal in the damaged and undamaged areas of a tube segment, resulting from an actual test in which the axial angle-beam pitch-catch technique of the invention was used, is illustrated by FIGS. 3 and 4. The test indicated that an average relative decrease of 6 dB in signal amplitude with a transducer separation of 1¼ inches.

Similarly, a circumferential arrangement of shearwave angle-beam transducers 20, 22 can be employed wherein the transducers are circumferentially aligned and spaced as illustrated in FIG. 2. The transmitting transducer 20 is energized to transmit shear-waves along a path 28 into the tube 24. Forty-five degree shear-wave wedges are preferred. The ultrasonic pulse is received by the receiving transducer 22. The circumferentially spaced transducers 20, 22 should be positioned about the tube by less than 180-degrees.

Testing has indicated that there is little change in relative attenuation over a test frequency of 2.25 MHz to 10 MHz. Especially good results are obtainable at a frequency of 5 MHz.

The surface of the tube to be inspected must be cleaned to a shiny metal condition and an adequate amount of couplant with low attenuation properties must be provided between the transducers and the tube surface in order to obtain meaningful attenuation measurements. A coupling marketed under the tradename Ultragel II, by Johnson & Johnson, Louistown, Pennsylvania, has been found to be suitable.

Thus, in both the axial and circumferential anglebeam pitch-catch technique, an ultrasonic pulse of shearwaves is transmitted into the wall of a boiler tube through a predetermined path. The pulse is received at the end of the path. The relative attenuation of the amplitude of the received pulse is then compared with a reference relative attenuation for an undamaged tube to detect the presence of hydrogen damage. The measurement and comparison can be accomplished by appropriate instrumentation automatically, for example, a Krautkramer Branson USL-38 pulser/receiver manufactured by K.B. Aerotech, Louistown, Pa. has been used.

Although the method of the invention has been described above in connection with the use of dual shearwave angle-beam transducers of the type which will typically embody a piezoelectric crystal, it is possible to employ an electromagnetic acoustic transducer to practice the invention.

Figure 5:
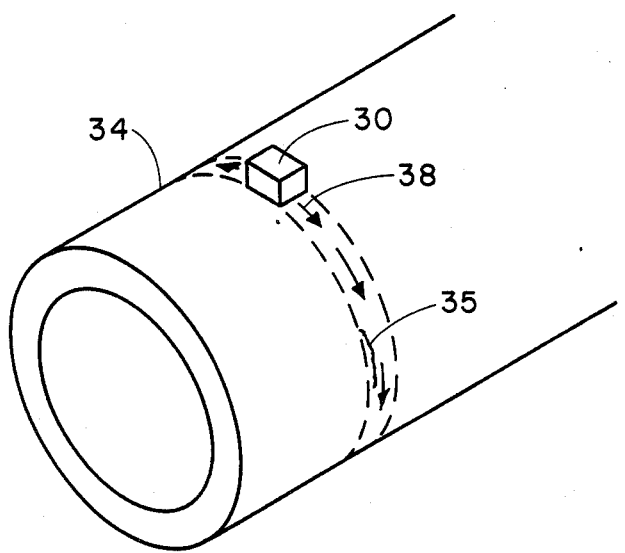
FIG. 5 is a schematic representation of the mounting of an electromagnetic acoustic transducer and a sound path of an ultrasonic pulse transmitted and received thereby to carry out the method of the invention.

As shown in FIG. 5, an electromagnetic acoustic transducer 30 is utilized to introduce an angle-beam shearwave into a boiler tube 34 through a sound path 38 to detect hydrogen damage 35. The wave travels 360-degrees, circumferentially, around the boiler tube 34. The relative attenuation of the received signal by a hydrogen damaged area is compared to the relative attenuation of an undamaged area to detect hydrogen damage. Use of a 0.45 MHz, center frequency, meander coil electromagnetic acoustic transducer has yielded favorable results. The use of an EMAT eliminates the need for couplant. In addition, excessive surface cleanliness is not needed.

The invention claimed is:

1. A method of ultrasonically testing a wall of a boiler tube for detecting hydrogen damage comprising the steps of:

providing a shear-wave angle-beam transmitting transducer with a frequency in the range of 2.5 MHz to 10 MHz at a first position on the outside surface of the boiler tube at a predetermined beam angle of forty-five degrees relative to the tube surface;

providing a shear-wave angle-beam receiving transducer with a frequency in the range of 2.5 MHz to 10 MHz at a second position on the outside surface of the boiler tube, said second position being circumferentially spaced from and aligned with said first position, and at a predetermined beam angle of forty-five degrees relative to the tube surface;

providing an adequate amount of couplant with low attenuation properties between said transducers and said outer surface of the boiler tube;

transmitting an ultrasonic pulse of shear-waves of a frequency in the range of 2.5 MHz to 10 MHz into the wall of the boiler tube from the transmitting transducer to the receiving transducer along a predetermined circumferential path;

measuring the relative attenuation of the amplitude of the received ultrasonic pulse; and comparing the relative attenuation of the amplitude of the received ultrasonic pulse with a known reference attenuation from an undamaged tube that does not have hydrogen damage to determine the presence of hydrogen damage.

2. A method as claimed in claim 1, wherein the transducers have a frequency of 5 MHz and the transmitted ultrasonic pulse has a frequency of 5 MHz.

3. A method of ultrasonically testing a wall of a boiler tube for detecting hydrogen damage comprising the steps of:

providing a shear-wave angle beam transmitting transducer with a frequency in the range of 2.5 MHz to 10 MHz at a first position on the outside surface of the boiler tube at a predetermined beam angle of sixty degrees relative to the tube surface;

providing a shear-wave angle beam receiving transducer with a frequency in the range of 2.5 MHz to 10 MHz at a second position on the outside surface of the boiler tube, said second position being axially aligned with and longitudinally spaced from said first position, and at a predetermined beam angle of sixty degrees relative to the tube surface;

providing an adequate amount of couplant with low attenuation properties between said transducers and said outside surface of the boiler tube;

transmitting an ultrasonic pulse of shear-waves of a frequency in the range of 2.5 MHz to 10 MHz into the wall of the boiler tube from the transmitting transducer to the receiving rransducer along a predetermined axial path;

measuring the relative attenuation of the amplitude of the received ultrasonic pulse; and comparing the relative attenuation of the amplitude of the received ultrasonic pulse with a known reference attenuation from an undamaged tube that does not have hydrogen damage to determine the presence of hydrogen damage.

4. A method as claimed in claim 3, wherein the transducers have a frequency of 5 MHz and the transmitted ultrasonic pulse has a frequency of 5 MHz.

5. A method as claimed in claim 3, wherein the boiler tube includes tube segments and a weld joining the segments and wherein the method further comprises positioning the transmitting and receiving transducers at an equally spaced distance beyond opposite sides of the weld.

6. A method of ultrasonically testing a wall of a boiler tube for detecting hydrogen damage comprising the steps of:

providing a 0.45 MHz, center frequency, meander coil electromagnetic acoustic transducer on the outer surface of the boiler tube;

energizing the electromagnetic acoustic transducer so as to introduce into the wall of the boiler tube an ultrasonic angle-beam shear-wave pulse which travels 360 degrees circumferentially around the wall of the boiler tube and which is then received by the electromagnetic acoustic transducer;

measuring the relative attenuation of the amplitude of the received ultrasonic pulse; and comparing the relative attenuation of the amplitude of the received ultrasonic pulse with a known reference attenuation from an undamaged tube that does not have hydrogen damage to determine the presence of hydrogen damage.

* * * * *